US008182821B2

(12) United States Patent
Pietersz et al.

(10) Patent No.: US 8,182,821 B2
(45) Date of Patent: May 22, 2012

(54) FLU VACCINE ADMIXTURE OF MANNAN AND FLU ANTIGEN

(75) Inventors: Geoffrey Allan Pietersz, Victoria (AU); Sandra Elizabeth Esparon, Victoria (AU); Owen Proudfoot, Victoria (AU)

(73) Assignee: The MacFarlane Burnet Institute for Medical Research and Public Health Ltd. (AU)

( * ) Notice: Subject to any disclaimer, the term of this patent is extended or adjusted under 35 U.S.C. 154(b) by 353 days.

(21) Appl. No.: 12/443,048

(22) PCT Filed: Oct. 2, 2007

(86) PCT No.: PCT/AU2007/001460

§ 371 (c)(1), (2), (4) Date: Aug. 18, 2009

(87) PCT Pub. No.: WO2008/037033

PCT Pub. Date: Apr. 3, 2008

(65) Prior Publication Data

US 2010/0008951 A1 Jan. 14, 2010

(30) Foreign Application Priority Data

Sep. 29, 2006 (AU) ................................ 2006222717

(51) Int. Cl.
*A61K 39/145* (2006.01)

(52) U.S. Cl. .................................................... 424/209.1

(58) Field of Classification Search ........................ None
See application file for complete search history.

(56) References Cited

U.S. PATENT DOCUMENTS

2004/0043032 A1 * 3/2004 McKenzie et al. ......... 424/184.1

FOREIGN PATENT DOCUMENTS

| | | |
|---|---|---|
| AU | 620149 | 3/1990 |
| EP | 0659768 | 6/1995 |
| WO | WO 95/18145 | 7/1995 |
| WO | WO 97/11715 | 4/1997 |
| WO | WO 97/11963 | 4/1997 |
| WO | WO 98/28003 | 7/1998 |
| WO | WO 99/16455 | 4/1999 |
| WO | WO 99/17783 | 4/1999 |
| WO | WO 99/55715 | 11/1999 |
| WO | WO 00/50078 | 8/2000 |
| WO | WO 01/57068 | 8/2001 |
| WO | WO 01/93912 | * 12/2001 |

OTHER PUBLICATIONS

Stambas et al ("Oxidised mannan as a novel adjuvant inducing mucosal IgA production," Vaccine 20:1068-1078, 2002).*

International Search Report prepared by the Australian Patent Office on Dec. 19, 2007, for International Application PCT/AU2007/001460.

Bork P et al., "The SEA module: A new extracellular domain associated with *O*-glycosylation." Protein Science 4:1421-1425 (1995).

Lett E et al., "Mucosal Immunogenicity of Polysaccharides Conjugated to a Peptide or Multiple-Antigen Peptide Containing T- and B-Cell Epitopes." Infection and Immunity 63(7):2645-2651 (1995).

McKenzie, I F C et al., "Oxidised mannan antigen conjugates preferentially stimulate T1 type immune responses." Veterinary Immunology and Immunopathology, 63(1-2):185-190 (1998).

Apostolopoulos, V et al., "Cell-mediated immune responses to MUC1 fusion protein coupled to mannan." Vaccine 14(9):930-938 (1996).

Pietersz G A et al., "Definition of MHC-restricted CTL epitopes from non-variable number of tandem repeat sequence of MUC1." Vaccine 18:2059-2071 (2000).

Sasaki S et al., "Human immunodeficiency virus type-1-specific immune responses induced by DNA vaccination are greatly enhanced by mannan-coated diC14-amidine." Eur J Immunol 27:3121-3129 (1997).

Stambas J et al., "Oxidised mannan as a novel adjuvant inducing mucosal IgA production." Vaccine 20(7-8):1068-1078 (2002).

Toda S et al., "HIV-1-specific cell-mediated immune responses induced by DNA vaccination were enhanced by mannan-coated liposomes and inhibited by anti-interferon-γ antibody." Immunology 92:111-117 (1997).

Vaughan H A et al., "Induction of humoral and cellular responses in cynomolgus monkeys immunized with mannan-human MUC1 conjugates." Vaccine 17(20-21):2740-2752 (1999).

Apostolopoulos V et al., "Aldehyde-mannan antigen complexes target the MHC class I antigen-presentation pathway." Eur J Immunol 30, 1714-1723 (2000).

Apostolopoulos V et al., "CTL in Mice Immunized with Human Mucin 1 Are MHC-Restricted." J Immunol 155:5089-5094 (1995).

Apostolopoulos V et al., "Oxidative/reductive conjugation of mannan to antigen selects for $T_1$ or $T_2$ immune responses." Proc Natl Acad Sci U S A 92:10128-10132 (1995).

Karanikas V et al., "Antibody and T Cell Responses of Patients with Adenocarcinoma Immunized with Mannan-MUC1 Fusion Protein." J Clin Invest 100:2783-2792 (1997).

Written Opinion for International (PCT) Patent Application No. PCT/AU2007/001460, mailed Jan. 3, 2008.

De Clercq "Recent highlights in the development of new antiviral drugs." Current Opinion in Microbiology, Oct. 2005, vol. 8, No. 5, pp. 552-560.

Joseph et al. "A new intranasal influenza vaccine based on a novel polycationic lipid—ceramide carbamoyl-spermine (CCS): I. Immunogenicity and efficacy studies in mice." Vaccine, May 2006, vol. 24, No. 18, pp. 3990-4006.

Supplementary Search Report for European Patent Application No. 07815271.7, dated Jan. 3, 2012, 7 pages.

* cited by examiner

*Primary Examiner* — Mary E Mosher
(74) *Attorney, Agent, or Firm* — Sheridan Ross P.C.

(57) ABSTRACT

The present invention relates to a vaccine composition comprising a carbohydrate polymer comprising mannose and flu antigen(s) (e.g. whole inactivated influenza virus) in admixture, and a method of immunising a subject comprising the step of administering the vaccine composition to a subject.

20 Claims, 13 Drawing Sheets

Flu: Alone Mixed Conjugated

Sera assayed 5 days after 2nd immunisation

Flu: Alone Mixed Conjugated

Sera assayed 5 days after 2nd immunisation

Assayed 7 days after 3rd immunisation

FLU VACCINE ADMIXTURE OF MANNAN AND FLU ANTIGEN

CROSS REFERENCE TO RELATED APPLICATIONS

This application is a national stage application under 35 U.S.C. 371 of PCT Application No. PCT/AU2007/001460 having an international filing date of 02 Oct. 2007, which designated the United States, which PCT application claimed the benefit of Australian Application No. 2006222717 filed 29 Sep. 2006, the entire disclosure of each of which are hereby incorporated herein by reference.

FIELD OF THE INVENTION

The present invention relates to a vaccine composition comprising a carbohydrate polymer comprising mannose and influenza virus (flu) antigen(s) (e.g. whole inactivated flu), and a method of immunising a subject comprising the step of administering the vaccine composition to a subject.

INCORPORATION BY REFERENCE

This patent application claims priority from:

AU 2006222717 entitled "Improved vaccine" filed 29 Sep. 2006.

The entire content of this application is hereby incorporated by reference.

BACKGROUND OF THE INVENTION

Most infectious agents enter the body through mucosal membranes, and recent vaccine strategies have concentrated on the production of antibodies at these sites to block their entry. The stimulation of secretory immune responses, which includes mucosal IgA, the predominant antibody isotype in mucosal secretions with the capability to neutralise bacteria, bacterial products and viruses, is considered to be crucial to vaccine development [1-4]. Currently most vaccines delivered by injection are not efficient at inducing a mucosal response.

At present, the oral polio vaccine remains the only successful large-scale vaccine that gives protection at the mucosal level. It is a live vaccine whose attenuation was achieved empirically with the attendant risks of back-mutation. In contrast, immunisation with defined protein antigens would have many advantages, including safety in immunosuppressed individuals. However, before such vaccines can be developed there is a need for adjuvants and delivery systems to overcome the problems associated with mucosal vaccination using defined protein antigens, including poor immunogenicity or the induction of tolerance.

Bacterial enterotoxins such as cholera toxin (CT) produced by Vibrio cholerae, and labile toxins from Escherichia coli have been co-administered with antigens and act as adjuvants with antigens [5,6]. However, these adjuvants pose health risks due to their toxic properties, and for the most part, cannot be used in human trials, and have limited usefulness for human vaccination.

Vaccines containing DNA encoding an antigen and low-viscosity carboxymethylcellulose sodium salt (CMCS-L) as a vehicle to carry the DNA to a site of action, have also been studied [7]. Lipids, such as monophosphoryl lipid A (CMPL) [8] which presumably aids in uptake of the antigen by the mucosal cell membrane, have also been used. However, the usefulness of these as adjuvants is unclear.

Adjuvants which have been administered with immunogens via the mucosa have therefore consisted of potentially dangerous bacterial or viral derivatives and display variable degrees of adjuvanticity.

The development of efficacious mucosal vaccines has further been hindered by incomplete understanding of mechanisms of pathogen transmission, and the immune responses specific to each pathogen. For example, development of a potent mucosal HIV vaccine has been affected by lack of understanding of mucosal HIV infection, and the immune responses that control the infection. There are studies which show that passive administration of IgG can confer protection against HIV infection at a mucosal site. However, the protection is limited, in that it appears unlikely that the protection is totally via neutralisation of the initial cell infection. It seems more likely that neutralisation at secondary lymphoid sites are important in controlling pathogen transmission via the mucosa [9]. Thus, many different approaches have been tried, to induce mucosal immunoglobin based immunity—like by immunising systematically and by immunising at a mucosal site. In most cases, the approaches have failed and are either toxic, or do not give rise to efficacious and practical immunoglobin based immune response.

Mannan, a polymannose or polysaccharide derived from the cell wall of yeast, when oxidised and conjugated to human Mucin 1 (an overexpressed cancer antigen) has been used in mice to induce immune responses [10, 11]. Intraperitoneal immunisation resulted in the induction of cellular immune responses as shown by production of cytotoxic T lymphocytes (CTLs) and their precursors, Th1 cytokines IFN-γ and IL-12. Antibody production was usually low. In tests in more than 100 patients, mannan has not shown any obvious toxicity or autoimmunity [12].

Mannose receptors which bind mannan have so far been identified on macrophages and dendritic cells. Oxidised mannan has been shown to stimulate production of IL-12 in macrophages, and also to stimulate T-cells, and to cause rapid trafficking of antigens to the class I pathway to produce cytotoxic T-cells in mice [13].

Surprisingly, the present applicant has discovered that if a carbohydrate polymer such as mannan is administered via a mucosal site (e.g. by intranasal administration), beneficial immunogenic effects are produced. In particular, when administered in admixture with an antigen from an influenza virus (flu) such as a whole inactivated flu, influenza-specific mucosal IgA and/or serum IgG immune responses can be produced. Moreover, when administered intramuscularly (i.m.), such an admixture of mannan and a flu antigen elicited a strong IgG immune response.

SUMMARY OF THE INVENTION

In a first aspect, the present invention provides a vaccine composition comprising a carbohydrate polymer comprising mannose and influenza virus (flu) antigen(s) in admixture.

The flu antigen(s) may be derived from human or animal influenza viruses (e.g. avian flu and equine flu). The flu antigen (s) is preferably selected from whole inactivated influenza virus (e.g. whole inactivated strain H1N1 flu virus).

The carbohydrate polymer comprising mannose is preferably a carbohydrate polymer comprising mannan, more preferably oxidised mannan.

Preferably, the vaccine composition is adapted to be administered at a mucosal site.

In a second aspect, the present invention provides a method of immunising a subject, comprising the step of administering a composition comprising a carbohydrate polymer comprising mannose and influenza virus antigen(s) in admixture.

Preferably, the step of administering the composition involves administration through a mucosal site (e.g. intranasal (i.n.) administration), but other routes, and particularly intramuscular (i.m.) administration, are also suitable.

The subject immunised may be a human or other animal.

In a third aspect, the present invention resides in the use of a carbohydrate polymer comprising mannose and influenza virus antigen(s) in the preparation of an admixture vaccine composition for immunising a subject.

In a particularly preferred embodiment of the present invention, the vaccine composition comprises a carbohydrate polymer comprising mannose (preferably mannan) and a limited (i.e. antigen- or dosage-sparing) amount of flu antigen(s) (preferably, whole inactivated strain H1N1 or H51N influenza virus) in admixture.

DETAILED DESCRIPTION OF THE INVENTION

Figure 1:
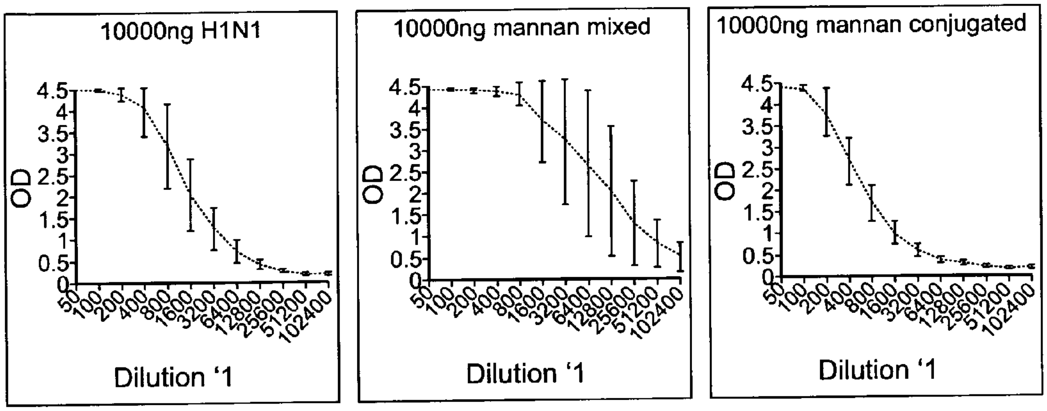
FIG. 1 shows IgG levels in mice when intranasally administered 10 μg dose of strain H1N1 influenza (flu) virus alone, flu virus and mannan admixture, and flu virus-mannan conjugate.

In a first aspect, the present invention provides a vaccine composition comprising a carbohydrate polymer comprising mannose and influenza virus (flu) antigen(s) in admixture.

By the term “admixture”, it is to be understood that the composition simply comprises a mixture such that there is no covalent linkage between the carbohydrate polymer and the antigen(s).

The flu antigen(s) may be derived from human or animal influenza viruses (e.g. avian flu and equine flu).

The flu antigen (s) is preferably selected from whole inactivated influenza (flu) virus, attenuated flu preparations, and specific antigenic flu polypeptides (e.g. for “subunit” vaccine compositions), or antigenic or epitope-containing fragments thereof.

Particular whole inactivated influenza viruses suitable for use in the present invention include whole inactivated strain H1N1 influenza virus and whole inactivated strain H5N1 influenza virus.

Particular antigenic flu polypeptides suitable for use in the present invention include haemagglutinin (Ha) polypeptides (e.g. Ha from human, avian or equine flu).

An antigenic flu polypeptide, or antigenic or epitope-containing fragment thereof, may form part of a fusion protein or polypeptide in order to, for example, act as a carrier and/or facilitate expression and purification upon production of the fusion protein in recombinant host cells. The non-antigen portion of the fusion protein would generally represent the N-terminal region of the fusion protein or polypeptide with the C-terminal sequences comprising the flu sequences. Fusion proteins and polypeptides may be selected from glutathione- S-transferase, β-galactosidase, or any other protein or part thereof, particularly those which enable affinity purification utilising the binding or other affinity characteristics of the protein (or part thereof) to purify the resultant fusion protein or polypeptide. The nature of the fusion protein or polypeptide will depend upon the vector system in which fusion proteins are produced. An example of a bacterial expression vector is pGEX which upon subcloning of a flu sequence of interest, produces a fusion protein consisting of glutathione-S-transferase with the flu polypeptide or peptide. Examples of other vector systems which give rise to fusion proteins are described in Sambrook et al., “Molecular Cloning: A Laboratory Manual”, Cold Spring Harbor Press, United States of America, 1989, incorporated herein in its entirety by reference.

The carbohydrate polymer comprising mannose is most preferably a carbohydrate polymer comprising mannan. In a preferred embodiment, the carbohydrate polymer is oxidised mannan (as described in WO 95/18145, which is hereby incorporated in its entirety by reference). The mannan is preferably isolated from the cell wall of yeast, and may be oxidised using reagents such as sodium periodate to produce a polyaldehyde. Reduced mannan may also be used, and a composition comprising reduced mannan may be prepared by adding sodium borohydride to an oxidised mannan.

The amount (by weight) of the mannan relative to the flu antigen(s) may be in the range of 3:1 to 250:1, preferably 5:1 to 120:1, and more preferably 10:1 to 100:1.

Preferably, the vaccine composition is adapted to be administered at a mucosal site. For example, the vaccine composition may be formulated for administration at a mucosal site by inhalation, through spraying the vaccine composition (e.g. an aerosol formulation) into the nasal region. However, the vaccine composition may also be formulated as droplets or fluid placed onto, or applied to, one or more mucosal sites such as regions of the mouth, tongue, throat, the gut including the stomach, the nasal and respiratory passages including the lungs, the reproductive tract including the vagina and cervix, and the rectum. In other embodiments, the vaccine composition may also be by formulated as a cream or balm for administration through rubbing or massaging onto one or more accessible mucosal sites. Further, the vaccine composition may also be formulated as a slow- or time-release device such as a capsule or a suppository (e.g. those based on alginate microspheres, poly(lactide-co-glycolide) or collagen polymers) which may be inserted, for example, in the rectum. Moreover, the vaccine composition may also be formulated for administration through injection into a mucosal site.

The vaccine composition may further comprise other adjuvants, pharmaceutically acceptable carriers, diluents or auxiliaries which may enhance the immunogenicity or effectiveness of the vaccine composition.

The vaccine composition may be provided in accordance with the manner in which it is to be administered. For example, the vaccine composition may be provided in a spray-container, aerosol can or nebuliser for intranasal administration by inhalation. Alternatively, the vaccine composition may be provided in a dropper bottle to enable dropwise administration of a solution or liquid formulation of the composition (e.g. to the oral cavity or throat for absorption).

In a second aspect, the present invention provides a method of immunising a subject, comprising the step of administering a composition comprising a carbohydrate polymer comprising mannose and influenza virus antigen(s) in admixture.

Preferably, the step of administering the composition involves administration through a mucosal site (e.g. intranasal (i.n.) administration), but other routes, and particularly intramuscular (i.m.) administration, are also suitable.

The immunisation may result in a cellular immune response against influenza virus, but preferably results in a humoral immune response against influenza virus. More preferably, the immunisation results in a humoral response wherein influenza-specific IgA antibody production (e.g. an IgA immune response) is stimulated, such that the titre of IgA at a selected mucosal area, and/or in the serum, is increased. In one embodiment, the IgA production following immunisation is greater when compared with production of IgG, IgM and IgE. In another embodiment, the immunisation results in greater production of IgA relative to the increase in IgG1 and/or IgG2a production. The levels of antibody may be increased in serum or at mucosal sites, or both.

A secretory IgA immune response against influenza virus at one or more mucosal sites can be particularly advantageous, because this can assist in the neutralisation of influenza virus upon entry into the body of the subject through mucosal membranes.

Administration of the vaccine composition at a mucosal site may involve administration at a region, or any area, of any mucosal surface (e.g. those lining the oral cavity or tissues, including the teeth and gingivae, those lining the gastrointestinal tract, or those lining the nasal passages and lungs, and the reproductive tract/tissues). The conjunctiva of the eyes also provides a suitable mucosal site for the administration of the vaccine composition. However, preferred examples of mucosal sites for administration of the vaccine composition are the respiratory tract such as the nasal region (i.e. intranasal (i.n.) administration), the trachea, bronchi and the lungs, the buccal or oral tissues including the oral (e.g. the mouth and gingivae) and oro-pharyngeal cavities, the throat including the tonsils, the gastrointestinal tract (e.g. oesophagus, stomach, duodenum, small and large intestines, colon and rectum).

The step of administering the vaccine composition may be conducted by a single event or multiple events, or may be part of a prime-boost protocol, a combination of these, or each of these with other, conventional methods of administration of a vaccine composition. The prime-boost protocol may, for example, comprise priming by intramuscular administration, and boosting by intranasal administration. The prime-boost may, in addition to the vaccine composition of the present invention, include DNA, viruses (e.g. vaccinia) or other immunogenic peptides or molecules, including the antigens described above. One or both of the priming and boosting composition may include the vaccine composition of the present invention. Thus, in a prime-boost protocol, one of the events may include the vaccine composition in accordance with the present invention, while the other may omit the carbohydrate polymer comprising mannose.

The amount and frequency that the vaccine composition is given to a subject may be routinely determined by an attending physician or veterinarian. However, by way of example, 1 μg to 10,000 μg/kg may be administered to a subject, preferably 5 μg to 5000 μg/kg, more preferably 8-1000 μg/kg and most preferably 400-600 μg/kg. Even more preferably, a dose of 100-200 μg/kg is contemplated, particularly for a human subject.

The vaccine composition may also be administered to a subject in conjunction with other immune regulators that lend themselves to efficacious administration via the mucosa. Further, the vaccine composition may also be administered with other adjuvants, pharmaceutically acceptable carriers, diluents or auxiliaries which may enhance the immunogenicity or effectiveness of the vaccine composition, or the vaccine composition may also be included therein, or be co- administered therewith. For example, lipofectamine may be co-administered with the vaccine composition of the invention.

The subject immunised may be a human or other animal. Thus, the invention may be used to prevent influenza in humans or other animals, especially mammals (e.g. livestock and companion animals).

Without wishing to be bound by any proposed mechanism for the observed advantages of the present invention, it is thought that the mannan not only acts as an adjuvant, but is also a potent mucosal adjuvant by virtue of increased or efficient uptake via the mucosa.

In a third aspect, the present invention resides in the use of a carbohydrate polymer comprising mannose and influenza virus antigen(s) in the preparation of an admixture vaccine composition for immunising a subject.

In a particularly preferred embodiment of the present invention, the vaccine composition comprises a carbohydrate polymer comprising mannose (preferably mannan) and a limited (i.e. antigen- or dosage-sparing) amount of flu antigen(s) (preferably, whole inactivated strain H51N influenza virus) in admixture. That is, it has been found that the vaccine composition of the present invention may comprise surprisingly low amounts of flu antigen(s) (e.g. amounts of $\leqq 2$ μg, more preferably 1 μg, even more preferably 0.5 μg, and most preferably 0.1 μg, to produce a strong influenza-specific IgA and/or IgG immune response. The use of dosage-sparing amounts of the flu antigen(s) may be particularly advantageous in the event of an influenza pandemic where only limited amounts of the flu antigen(s) may be available. The vaccine composition of the particularly preferred embodiment is preferably adapted to be administered intranasally. The vaccine composition of the particularly preferred embodiment also preferably comprises an amount (by weight) of the mannan relative to the flu antigen(s) in the range of 50:1 to 200:1, preferably 80:1 to 120:1, and more preferably about 100:1.

The invention will hereinafter be further described by way of the following non-limiting examples and figures.

EXAMPLES

Example 1

Materials and Methods

Mice

Female 6-8 week old (CBAxBALB/c)F1 and C57B1/10 mice were bred and maintained under conventional but infection-free conditions.

Preparation of Oxidised or Reduced Mannan-antigen Conjugates

Mannan (Sigma Chemical Co., St Louis, Mo., United States of America) was coupled to the antigens under oxidising conditions. Mannan at 14 mg/ml in 0.1 M phosphate buffer pH 6.0 was oxidised with 0.01 M sodium periodate for 60 min at 4° C. Ten microlitres of ethandiol (Sigma Chemical Co., St Louis, Mo., United States of America) was added to quench the reaction and the mixture incubated for 30 min at 4° C. This mixture was then passed through a PD-10 column (Pharmacia Biotech, Uppsala, Sweden) equilibrated with bicarbonate buffer pH 9.0. The oxidised mannan, eluted in the 2 ml void volume, was mixed with 700 μg of the antigen, incubated overnight at room temperature and used without any further purification. Conjugation was confirmed when the conjugates were separated using 12.5% sodium dodecyl sulphate-polyacrylamide gel electrophoresis (SDS-PAGE) and a heterogeneous smear (compared with the single band of uncoupled protein) was observed using Comassie Blue stain. For comparison in some experiments, the oxidised conjugates were reduced with sodium borohydride ($NaBH_4$) (Aldrich, Castle Hill, NSW, Australia) 1 mg/ml overnight at room temperature and used without further purification.

Preparation of Oxidised or Reduced Mannan and Antigen Admixtures

Flu virus and mannan admixtures were prepared by simply mixing the whole inactivated flu virus with an amount of mannan in solution. The amount of mannan to flu virus is typically 10:1, but preferably admixtures are prepared to provide a doasge unit comprising 100 μg of mannose regardless of the amount of flu virus.

Immunisation of Mice

Mice were lightly anaesthetised with penthrane and 50 μl of vaccine composition (i.e. flu antigen(s) mannan admixture or mannan-antigen conjugate) (12 μg antigen/mouse in bicarbonate buffer pH9.0, unless otherwise specified), placed onto the nares to be inhaled by the mouse. Unless stated otherwise, this procedure was performed on days 0, 10 and 17 of the experiments.

Collection of Samples

Serum samples were collected after mice were bled by cardiac puncture following euthanasia at the end of each experiment. For time-course experiments, mice were placed on a heat box, a small incision made in a lateral vein and 200 μl of blood collected with a micropippeter. The serum was subsequently separated by centrifugation. Lung washings were obtained after mice were euthanased with $CO_2$. Lungs were washed in situ with 0.5 ml PBS through an opening in the trachea. All samples were stored at −20° C. prior to assay.

Detection of Antibody in the Serum and Mucosal Sites by ELISA

Microtitre plates (Nunc Roskilde, Denmark) were coated overnight at 4° C. with 5 μg/ml antigen in carbonate buffer pH 9.1. The wells were then blocked with 2% foetal calf serum (FCS) (Trace Biosciences, Castle Hill, NSW, Australia) in PBS for 1 hour at 37° C. The plates were washed 3 times with 0.08% Tween 20 (BDH Laboratory Supplies, Poole, England) PBS and appropriately diluted samples in 50 μl added and incubated for 2 hours at room temperature. After two more washes, antigen-specific IgA was detected by the addition of an anti-mouse IgA affinity purified horse radish peroxidase (HRP) conjugate (Southern Biotechnology Associates Inc., Birmingham, United States of America) diluted 1/1000 in 0.1% bovine serum albumin (BSA) (CSL, Melbourne, Australia) for 1 hour at room temperature. Antigen specific IgG1 or IgG2a was detected with the addition of a biotinylated anti-mouse IgG1 or IgG2a conjugate (Caltag Laboratories, Burlinggame, Calif., United States of America) diluted 1/1000 in 0.1% BSA. The plates were washed twice more and a streptavidin peroxidase conjugate (Boehringer Mannheim, Mannheim, Germany) added at a 1/1000 dilution in 0.1% BSA. Following a further two washes, the antibody titres of all the subclasses tested were determined when the substrates containing either 0.4 g/l 3, 3', 5, 5'-tetramethylbenzidine (TMB) (Kirkgaard and Perry Laboratories, Gaithersburg, Md., United States of America) and 0.02% $H_2O_2$ or 2,2'-azino-bis(3-ethylbenthiazoline-6-sulphonic acid) (ABTS) (Sigma Chemical Co., St Louis, Mo., United States of America) and 0.03% $H_2O_2$ were added (50 μl/well). Plates were left 10 minutes for colour to develop and the reaction stopped with 2 M $H_2SO_4$ for the TMB substrate or 0.2 M citric acid for ABTS. OD at 450 nm (TMB) or 405 nm (ABTS) was read in an ELISA reader (Labsystems, Helsinki, Finland). Antibody titres were presented as the highest dilution which yielded an optical density at 450 nm or 405 nm >0.1 OD units higher than normal serum at 1/100 dilution. For calculation of means, the titre was converted to $\log_{10}$ and a geometric mean was derived.

Statistics

The statistical significance of data was determined by the two-sample ranks test (Wilcoxon-White) or by Student's t test based on the $\log_{10}$ titre. Differences with $p<0.05$ were considered significant.

Example 2

Human Influenza Strain H1N1

H1N1 was prepared along the lines set forth in Example 1. Inactivated H1N1 was obtained from the WHO collaborative centre, Melbourne (Victroia, Australia), and prepared according to Davenport et al. [14]. Briefly, the virus was grown in embryonated hen eggs and purified using standard conditions. The virus was inactivated with gamma-butyrolactone.

The various doses and modes of administration are shown below in Table 1:

TABLE 1

| | Groups: | |
|---|---|---|
| Intranasal immunisation | 1. Buffer alone (n = 4) | |
| | 2. 400 ng H1N1 alone (n = 5) | |
| | 3. 5000 ng H1N1 alone (n = 5) | |
| | 4. 10000 ng H1N1 alone (n = 5) | |
| | 5. 400 ng Mannan mixed (n = 5) | |
| | 6. 5000 ng Mannan mixed (n = 5) | |
| | 7. 10000 ng Mannan mixed (n = 5) | |
| | 8. 400 ng Mannan conjugated (n = 5) | |
| | 9. 5000 ng Mannan conjugated (n = 5) | |
| | 10. 10000 ng Mannan conjugated (n = 5) | |
| | 11. 10000 ng H1N1 alone IM (n = 4) | Intramuscular |
| | 12. 10000 ng Mannan mixed IM (n = 4) | (+'ve control) |
| | 13. 10000 ng Mannan conj' IM (n = 4) | immunisation |

Antibody levels were measured. At the 400 ng dose there was no enhancement of immunogenicity by mannan (admixture or conjugate) as shown by IgG levels. At the 5,000 ng dose the admixed flu virus mannan ("mannan mixed") showed unexpected enhancement in IgG. This was more pronounced at the 10,000 ng dose (i.e. 10 μg) as shown in FIG. 1.

Figure 2:
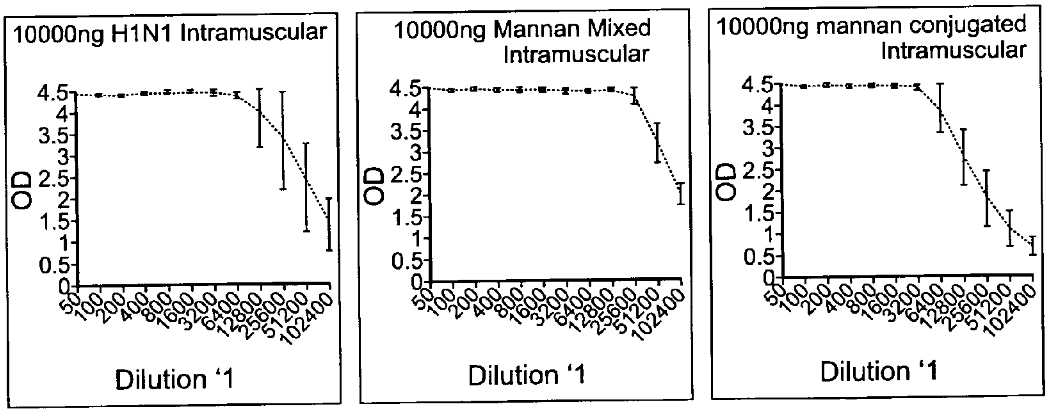
FIG. 2 shows IgG levels in controls involving intramuscular administration of strain H1N1 influenza (flu) virus alone, flu virus and mannan admixture, and flu virus-mannan conjugate.

FIG. 2 shows results from positive controls involving intramuscular administration. The observation was confirmed when serum IgG was tested after two immunisations 10 days apart (data not shown).

Figure 3:
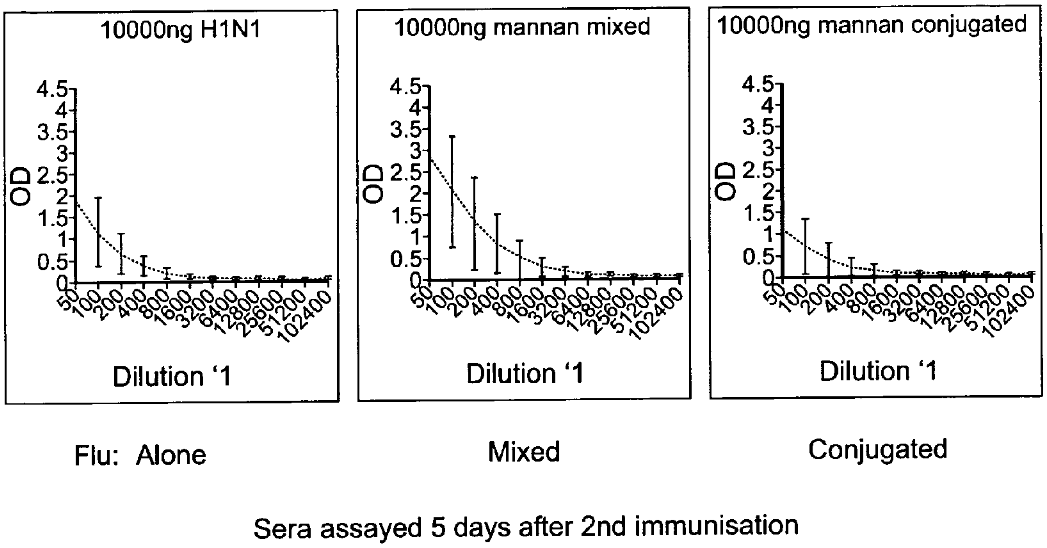
FIG. 3 shows IgA levels at 10 μg dose in mice when intranasally administered 10 μg dose of strain H1N1 influenza (flu) virus alone, flu virus and mannan admixture, and flu virus-mannan conjugate.
Figure 4:
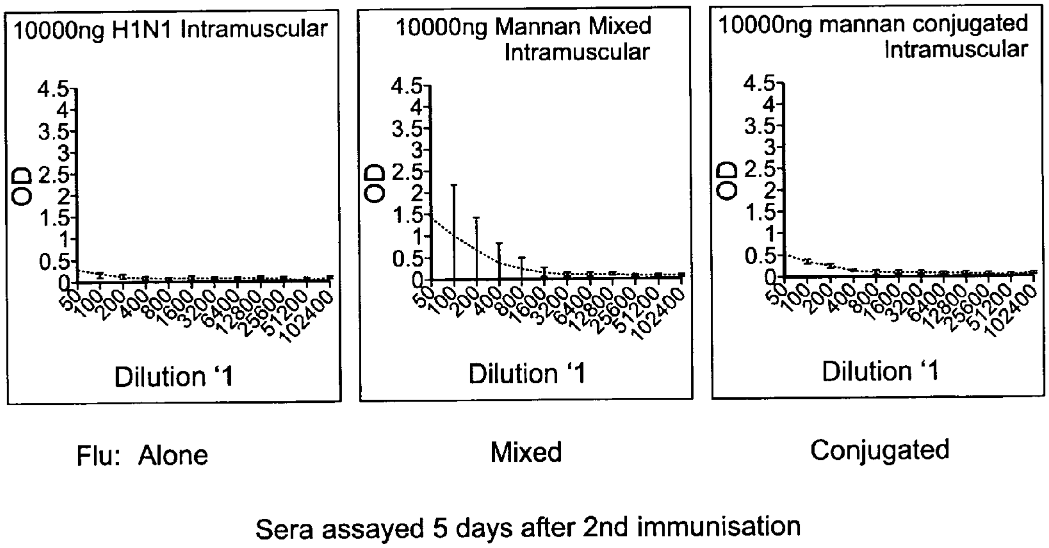
FIG. 4 shows IgA levels in controls involving intramuscular administration in the mice when intranasally administered 10 μg dose of strain H1N1 influenza (flu) virus alone, flu virus and mannan admixture, and flu virus-mannan conjugate.

The same serum was tested for IgA and provided surprising results. Similar to IgG levels discussed above, at the 400 ng dose there was no enhancement of immunogenicity. At the 5,000 ng dose, some enhancement of IgA levels was detectable, however, at 10,000 ng (10 μg) the flu virus mannan admixture provided the most IgA as shown in FIG. 3. In contrast to the intranasally administered mice, little or no IgA was induced by intramuscular administration (see FIG. 4). These results were confirmed by a third immunisation at day 17 (results not shown).

Figure 5:
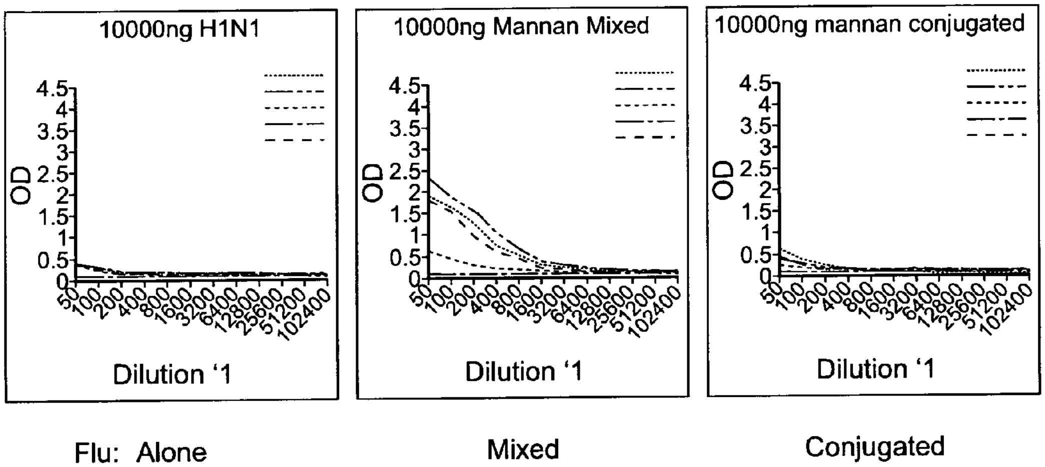
FIG. 5 shows IgA levels in lung washes of mice administered intranasally with 10 μg dose of strain H1N1 influenza (flu) virus alone, flu virus and mannan admixture, and flu virus-mannan conjugate.
Figure 6:
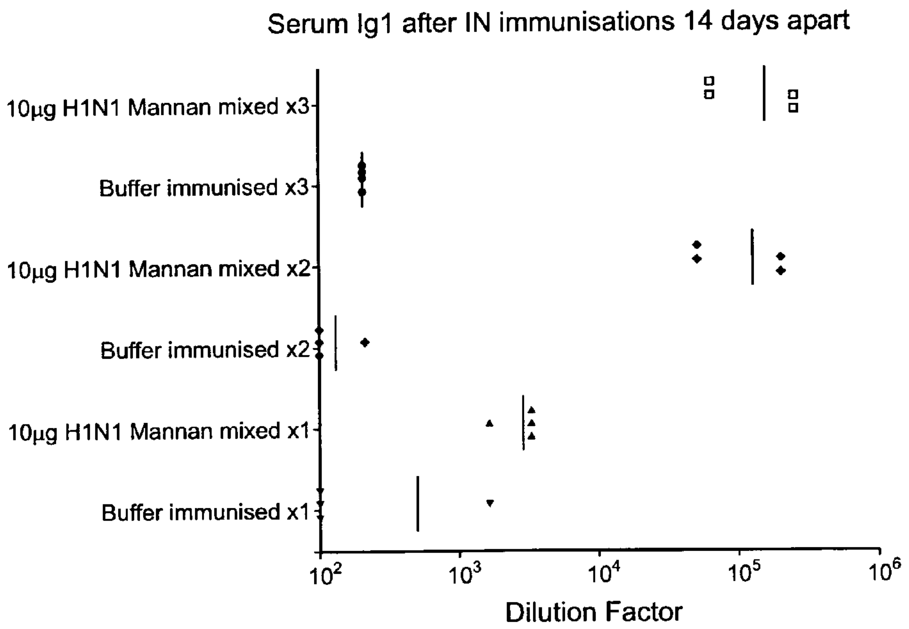
FIG. 6 shows serum IgG1 levels of mice administered intranasally with 10 μg dose of strain H1N1 influenza (flu) virus and mannan admixture 14 days apart.
Figure 7:
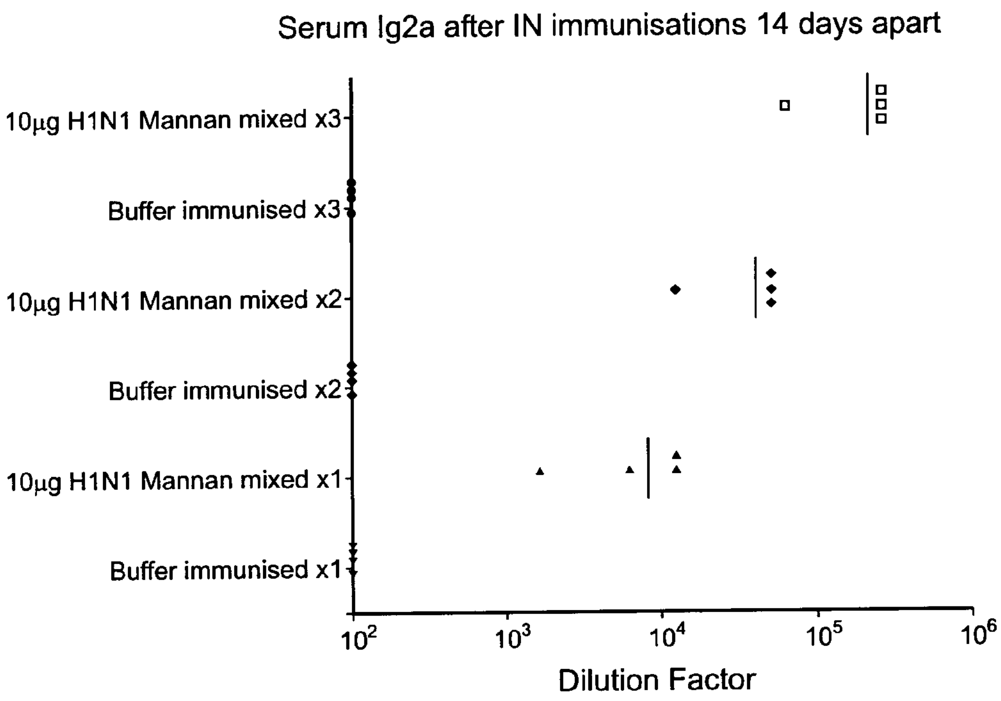
FIG. 7 shows IgG2a levels of mice administered intranasally with 10 μg dose of strain H1N1 influenza (flu) virus and mannan admixture 14 days apart.
Figure 8:
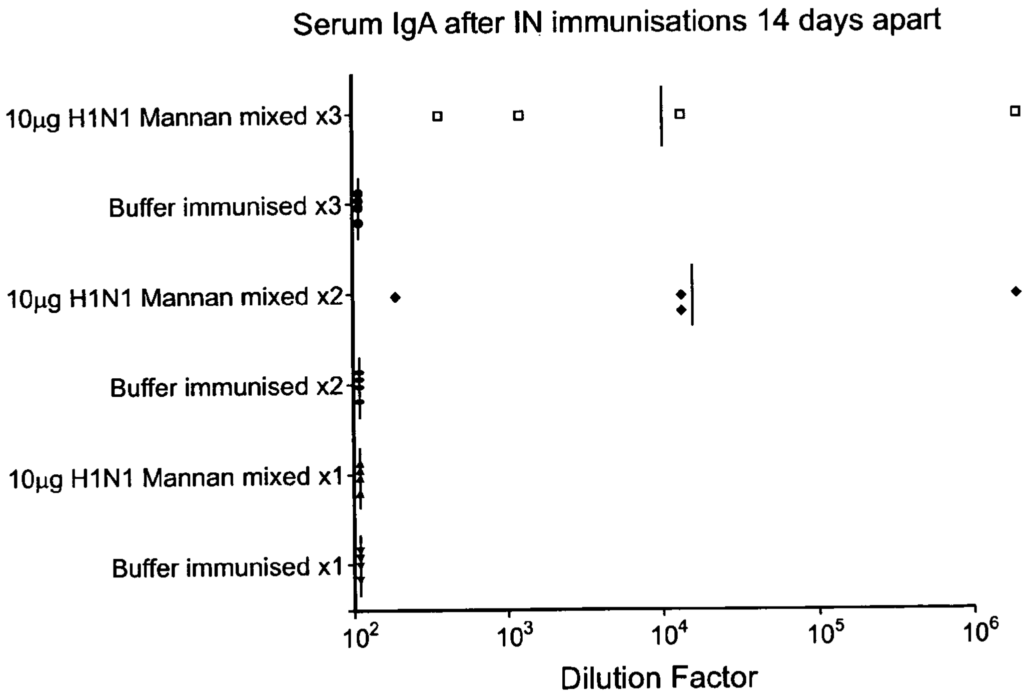
FIG. 8 shows IgA levels of mice administered intranasally with 10 μg dose of strain H1N1 influenza (flu) virus and mannan admixture 14 days apart.
Figure 9:
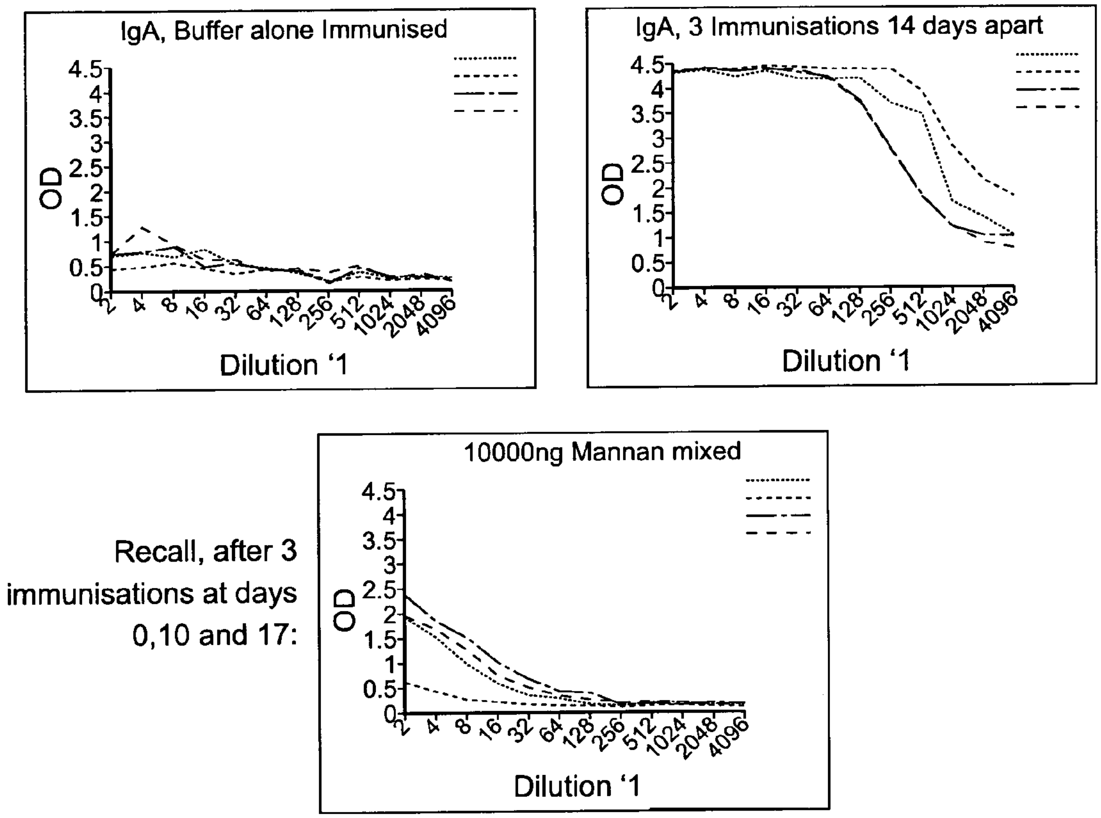
FIG. 9 shows results of IgA levels from lung washes of mice administered 3 times intranasally with 10 μg dose of strain H1N1 influenza (flu) virus and mannan admixture 14 days apart.

At the end of the third immunisation, lung washes were performed (mice were culled using drugs not $CO_2$ or cervical dislocation) and 700 to 1,000 μl of PBS was introduced then carefully recovered and assayed as described in Example 1. The flu virus mannan admixture showed superior results as seen in FIG. 5.

This example demonstrates that contrary to expectations, admixed flu virus and mannan outperformed mannan flu-virus conjugate in terms of IgG stimulation. As would be expected, intramuscular administration gave a greater IgG response in terms of total IgG produce in sera. However, the most surprising result was that the highest levels of IgA were induced by the admixed flu virus and mannan composition. Further, intranasal administration induced more IgA than intramuscular administration. A secretory IgA response in the lung was evident when admixed flu virus and mannan was administered by the intranasal route. However, in further experiments (data not shown), immunisation by intranasal administration of the flu virus and mannan admixture preferably involved two immunisations (two weeks apart), whereas high levels of serum IgG could be produced after a single intramuscular administration with the flu virus mannan admixture (although this did not result in any mucosal IgA). Further, it was surprisingly found that the single intramuscular administration could use as little as 0.1 μg of flu virus (strain H5N1 tested) to induce a strong serum IgG immune response.

Example 3

Further Experiments with 10 μg Admixed Flu Virus and Mannan

Experiments were conducted similar to Example 10 where mice received three immunisations 14 days apart (day 0, day 14 and day 28). The mice were bled on days 12, 26 and 35 and an analysis of serum antibody and IgA profiles were conducted including tests for IgG1 and IgG2a. At the conclusion, mice were sacrificed and a lung fluid wash was conducted to determine levels of secretory IgA. Results are shown in FIGS. 6 to 9.

This example demonstrates the extended time frame between doses yields multiple benefits in antibody responses. In particular, it demonstrates that admixed flu virus and mannan administered intranasally at three 14 days intervals to mice results in reasonable IgG1 and IgG2a titres more conveniently than the day 0, 10, 17 protocol. For example, IgG1 was boosted to $10^5$ after the second immunisation which was greater than the "total" IgG in the 0, 10, 17 day protocol. IgG2a was boosted to around $5\times10^4$ after the second immunisation and $10^5$ after the third immunisation.

The example also demonstrated that intranasal administration at three 14 day intervals of the admixed flu virus and mannan results in reasonable IgA titres and is a marked improvement over the shorter immunisation protocol. Similar end titres of IgA antibodies may be obtained by three immunisations at shorter intervals or by two immunisations at 14 days. The 14 day protocol resulted in vastly improved IgA in lung wash fluid than the 0, 10, 17 day protocol.

Example 4

Antibody Effectiveness as Determined by Haemagglutinin (HI) Assay

To determine whether the antibodies were protective, HI assays were conducted. This is a well known assay and followed the protocol using turkey or chicken red blood cells. The assay measures the ability of the sera from immunised mice to inhibit the virus binding to sugar residues on the red blood cells. A final dilution of sera (across a two-fold series dilution starting at 10 fold) that inhibits agglutination denotes the "HI titre" of the sample. A "HI titre" of 40 is considered protective.

Sera from the mice of Example 2 were used. Inactivated H5N1 was from the WHO collaborative centre, Melbourne. This virus was made by reverse genetics so that it can be grown in chicken eggs and inactivated as above. For the H5N1 in HI assays, live virus was used. The H5N1 is a modified H5N1 rather than the virulent H5N1 in that the polybasic site of the virulent strain has been removed. This also means that BL3 containment conditions do not have to be used with this virus.

Figure 10:
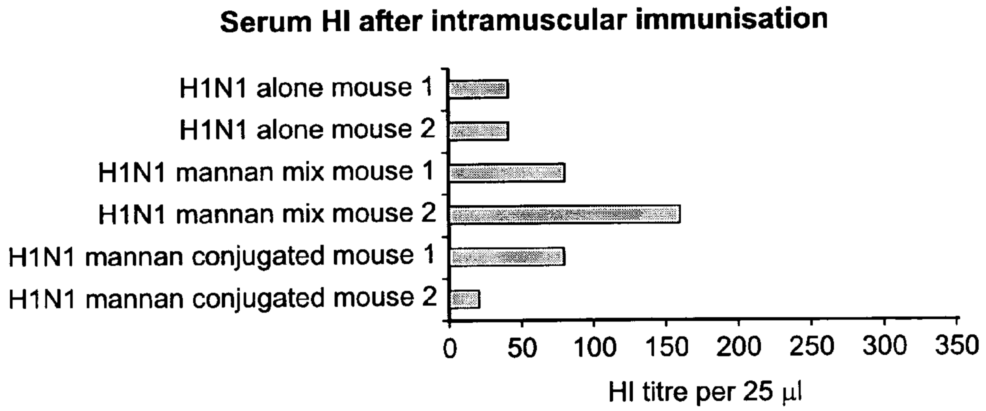
FIG. 10 shows serum HI after intramuscular injection of mice with strain H1N1 influenza (flu) virus alone, flu virus and mannan admixture, and flu virus-mannan conjugate.
Figure 11:
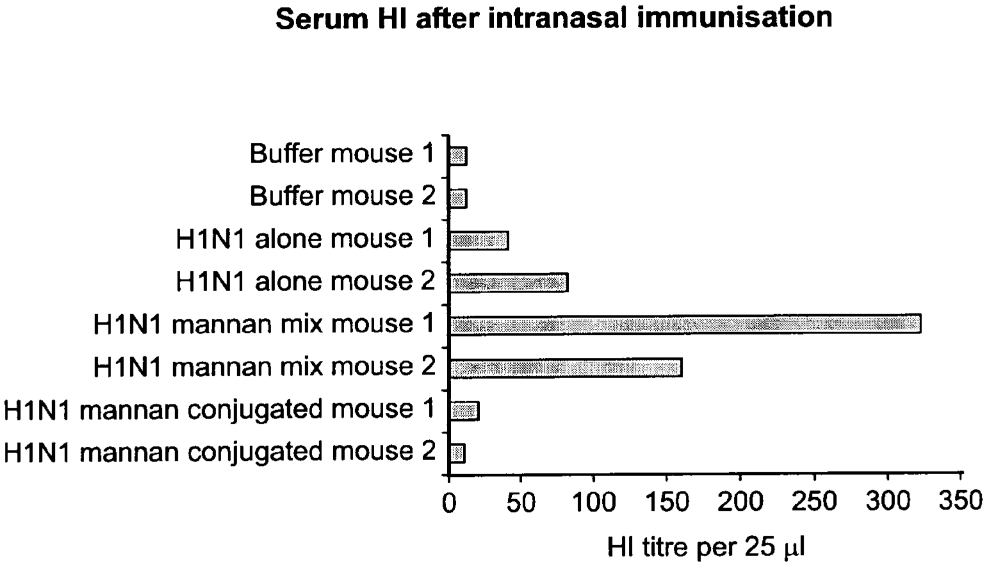
FIG. 11 shows serum HI after intranasal administration of mice with strain H1N1 influenza (flu) virus alone, flu virus and mannan admixture, and flu virus- mannan conjugate.

Results for intramuscular and intranasal administration are shown in FIGS. 10 and 11. These show that HI (i.e. protectivity of antibodies) may be greater when immunisation is intranasal, particularly when the antigen is in admixture with mannan.

Example 5

Antibodies Generated by Immunisation are Cross-reactive for H5N1

Sera was collected from mice separately immunised with bicarbonate buffer alone, 10 μg H1N1 alone, 10 μg H1N1-mannan admixture, 10 μg H1N1 conjugated with oxidised mannan and, as a positive control, rabbit anti-H1N1 polyclonal antibody (Burnet Institute, Melbourne, Victoria, Australia) similar to Example 2. Inactivated H1N1, H3N2 (from the WHO collaborative centre, Melbourne), H5N1 were run on an SDS-PAGE gel transferred to nitrocellulose and probed with the above anti-sera.

Figure 12:
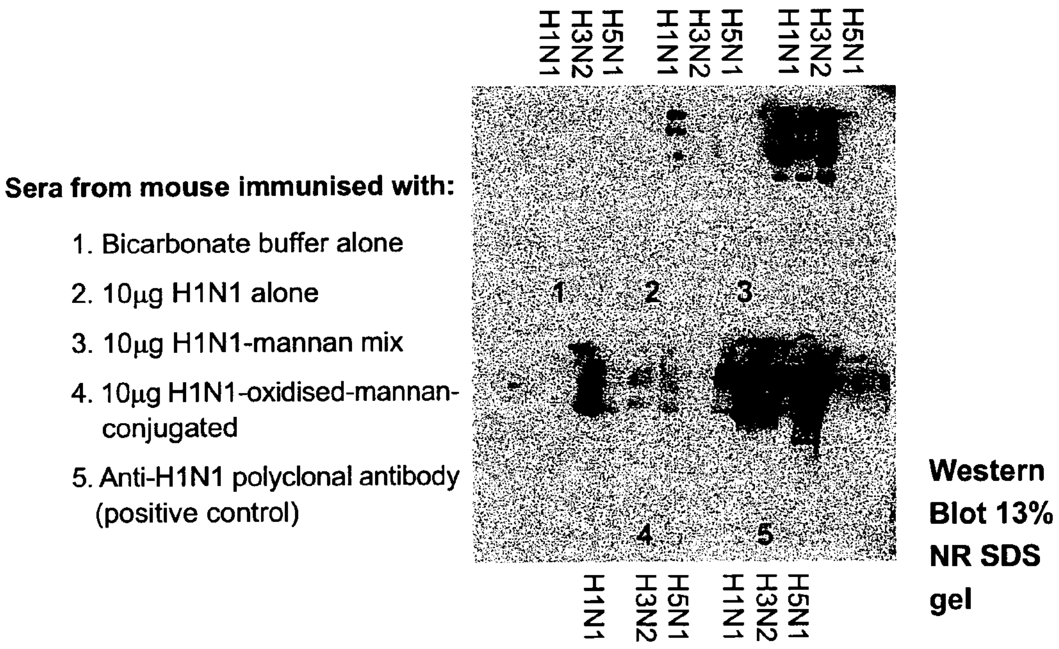
FIG. 12 shows a Western blot of gels showing that antibodies produced to strain H1N1 influenza (flu) virus are cross-reactive with strain H5N1 influenza (flu) virus.

The results presented in FIG. 12 show that antibodies generated by intranasal administration of H1N1 admixed with mannan are cross reactive with the avian flu strain H5N1. This is an extremely important observation as it indicates that mannan may be an important adjuvant in achieving protection against bird flu outbreaks in humans.

Example 6

Vaccination with H5N1 in Different Animals

Different animal models such as ferrets and mice may be used. Where ferrets are used, groups of 4 animals are lightly anaethetised and immunised intranasally with mannan conjugated to inactivated H5N1 virus, admixture of virus and mannan, virus alone and saline alone. Ferrets are observed daily for signs of illness and nasal washings collected every 3 days for 15 days post infection. To collect nasal washings ferrets are lightly anaesthetised and 0.5 ml PBS instilled into each nostril. The expelled liquid is collected, centrifuged and the supernatant used to assess viral titres and protein concentration.

Similarly mice are challenged with different doses of inactivated virus which are administered intranasally to groups of 5 to 8 mice on day 0, 14 and 28. 10 days after each immunisation mice are bled and sera collected and assayed for IgG2a, IgG1, IgM and IgA antibody against the H5N1 virus. If satisfactory titres are obtained some mice are euthanased after a further 10 days and lung washings isolated and tested for mucosal IgA. In addition other mice are challenged with live virus and survival rates, live weights and nasal washings are analysed.

Example 7

Use of "Split" H5N1 in Admixture with mannan in Intranasal Vaccination

In this example "split" H5N1 virus (i.e. fragmented virus) is used as above. The split virus is virus that has been dissociated into various subunits by sodium deoxycholate. The analysis of antibody titres is as above.

Example 8

Vaccination with H5N1

A trial was conducted that was similar to that envisaged by Example 6 above. HI assays were conducted in accordance with Example 4. The samples were as follows:

Samples 1 to 36 all=H1N1—New Caledonia trial-derived, tested against H1N1—New Caledonia.

Samples 37 to 66=H5N5—Vietnam trial-derived, tested against H5N1—Vietnam.

H="<10" means no H1 observed at all, even at dilution factor 10.

H1="actual 10" means H1 observed at dilution factor 10, but not beyond.

Note that the only "single immunisation" H1N1 trial sera tested were samples 33 to 36. The results are shown in Table 2 below:

TABLE 2

| HI_OP_002 Sample # | Influenza Strain | From Experiment # | Condition/ Timepoint | HI Titre |
|---|---|---|---|---|
| 1 | H1N1 NC | Flu_2 | Buffer × 2 | <10 |
| 2 | H1N1 NC | Flu_2 | 7 days after | <10 |
| 3 | H1N1 NC | Flu_2 | 2nd imm' | <10 |
| 4 | H1N1 NC | Flu_2 | Intranasal | <10 |
| 5 | H1N1 NC | Flu_2 | | <10 |
| 6 | H1N1 NC | Flu_2 | 10 ug H1N1 × 2 | <10 |
| 7 | H1N1 NC | Flu_2 | alone, 7 days | <10 |
| 8 | H1N1 NC | Flu_2 | after imm' | <10 |
| 9 | H1N1 NC | Flu_2 | Intranasal | <10 |
| 10 | H1N1 NC | Flu_2 | | <10 |
| 11 | H1N1 NC | Flu_2 | 10 ug H1N1 × 2 | 80 |
| 12 | H1N1 NC | Flu_2 | MIX, 7 days | ('actual')10 |
| 13 | H1N1 NC | Flu_2 | after imm' | 40 |
| 14 | H1N1 NC | Flu_2 | Intranasal | ('actual')10 |
| 15 | H1N1 NC | Flu_2 | | 20 |
| 16 | H1N1 NC | Flu_2 | 10 ug H1N1 × 2 | <10 |
| 17 | H1N1 NC | Flu_2 | CONJ', 7 days | <10 |
| 18 | H1N1 NC | Flu_2 | after imm' | <10 |
| 19 | H1N1 NC | Flu_2 | Intranasal | <10 |
| 20 | H1N1 NC | Flu_2 | | <10 |
| 21 | H1N1 NC | Flu_2 | 10 ug H1N1 × 2 | 40 |
| 22 | H1N1 NC | Flu_2 | alone, 7 days | 40 |
| 23 | H1N1 NC | Flu_2 | after imm' | 40 |
| 24 | H1N1 NC | Flu_2 | Intramuscular | 20 |
| 25 | H1N1 NC | Flu_2 | 10 ug H1N1 × 2 | 80 |
| 26 | H1N1 NC | Flu_2 | MIX, 7 days | 80 |
| 27 | H1N1 NC | Flu_2 | after imm' | 160 |
| 28 | H1N1 NC | Flu_2 | Intramuscular | 80 |
| 29 | H1N1 NC | Flu_2 | 10 ug H1N1 × 2 | 80 |
| 30 | H1N1 NC | Flu_2 | CONJ', 7 days | ('actual')10 |
| 31 | H1N1 NC | Flu_2 | after imm' | 40 |
| 32 | H1N1 NC | Flu_2 | Intramuscular | 20 |
| 33 | H1N1 NC | Flu_3 | 10 ug H1N1 × 1 | ('actual')10 |
| 34 | H1N1 NC | Flu_3 | MIX, 12 days | 40 |
| 35 | H1N1 NC | Flu_3 | after imm' | 80 |
| 36 | H1N1 NC | Flu_3 | Intranasal | 20 |
| 37 | H5N1 Viet' | Flu_4 | 10 ug H5N1 × 1 | 40 |
| 38 | H5N1 Viet' | Flu_4 | alone, 12 days | <10 |
| 39 | H5N1 Viet' | Flu_4 | after imm' | <10 |
| 40 | H5N1 Viet' | Flu_4 | Intranasal | <10 |
| 41 | H5N1 Viet' | Flu_4 | | 80 |
| 42 | H5N1 Viet' | Flu_4 | 10 ug H5N1 × 1 | 80 |
| 43 | H5N1 Viet' | Flu_4 | MIX, 12 days | 80 |
| 44 | H5N1 Viet' | Flu_4 | after imm' | <10 |
| 45 | H5N1 Viet' | Flu_4 | Intranasal | 80 |
| 46 | H5N1 Viet' | Flu_4 | | ('actual')10 |
| 47 | H5N1 Viet' | Flu_4 | 10 ug H5N1 × 1 | <10 |
| 48 | H5N1 Viet' | Flu_4 | CONJ', 12 days | ('actual')10 |
| 49 | H5N1 Viet' | Flu_4 | after imm' | 80 |
| 50 | H5N1 Viet' | Flu_4 | Intranasal | ('actual')10 |
| 51 | H5N1 Viet' | Flu_4 | | ('actual')10 |
| 52 | H5N1 Viet' | Flu_4 | 10 ug H5N1 × 2 | 40 |
| 53 | H5N1 Viet' | Flu_4 | alone, 12 days | 40 |
| 54 | H5N1 Viet' | Flu_4 | after imm' | 40 |
| 55 | H5N1 Viet' | Flu_4 | Intranasal | 80 |
| 56 | H5N1 Viet' | Flu_4 | | 80 |
| 57 | H5N1 Viet' | Flu_4 | 10 ug H5N1 × 2 | 80 |
| 58 | H5N1 Viet' | Flu_4 | MIX, 12 days | 20 |
| 59 | H5N1 Viet' | Flu_4 | after imm' | 40 |
| 60 | H5N1 Viet' | Flu_4 | Intranasal | 80 |
| 61 | H5N1 Viet' | Flu_4 | | 80 |
| 62 | H5N1 Viet' | Flu_4 | 10 ug H5N1 × 2 | <10 |
| 63 | H5N1 Viet' | Flu_4 | CONJ', 12 days | ('actual')10 |

TABLE 2-continued

| HI_OP_002 Sample # | Influenza Strain | From Experiment # | Condition/ Timepoint | HI Titre |
|---|---|---|---|---|
| 64 | H5N1 Viet' | Flu_4 | after imm' | 20 |
| 65 | H5N1 Viet' | Flu_4 | Intranasal | <10 |
| 66 | H5N1 Viet' | Flu_4 | | <10 |

Figure 13:
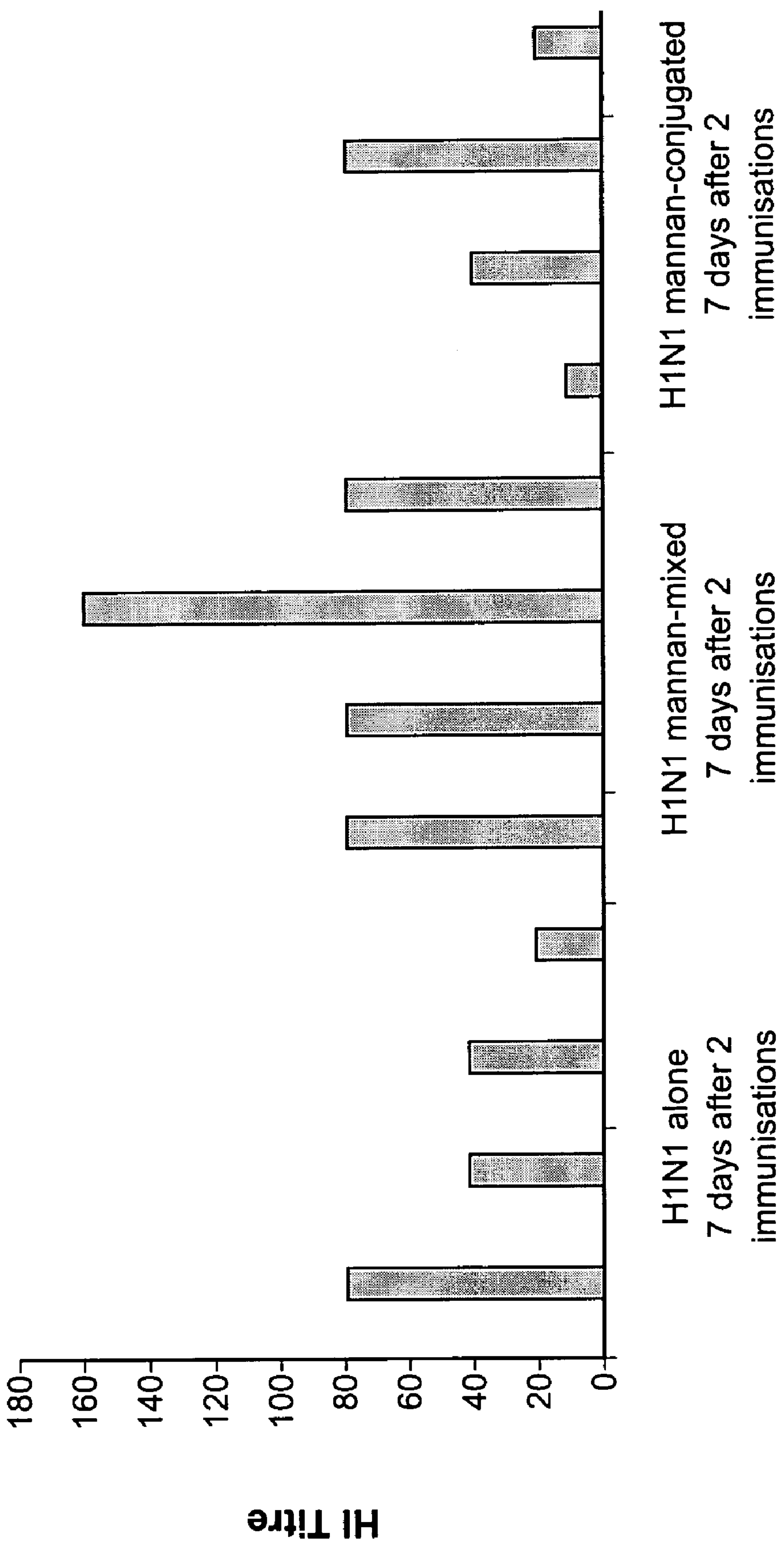
FIG. 13 shows HI titres in mice given two immunisations (7 days apart) with with strain H1N1 influenza (flu) virus alone, flu virus and mannan admixture, and flu virus-mannan conjugate.
Figure 13:
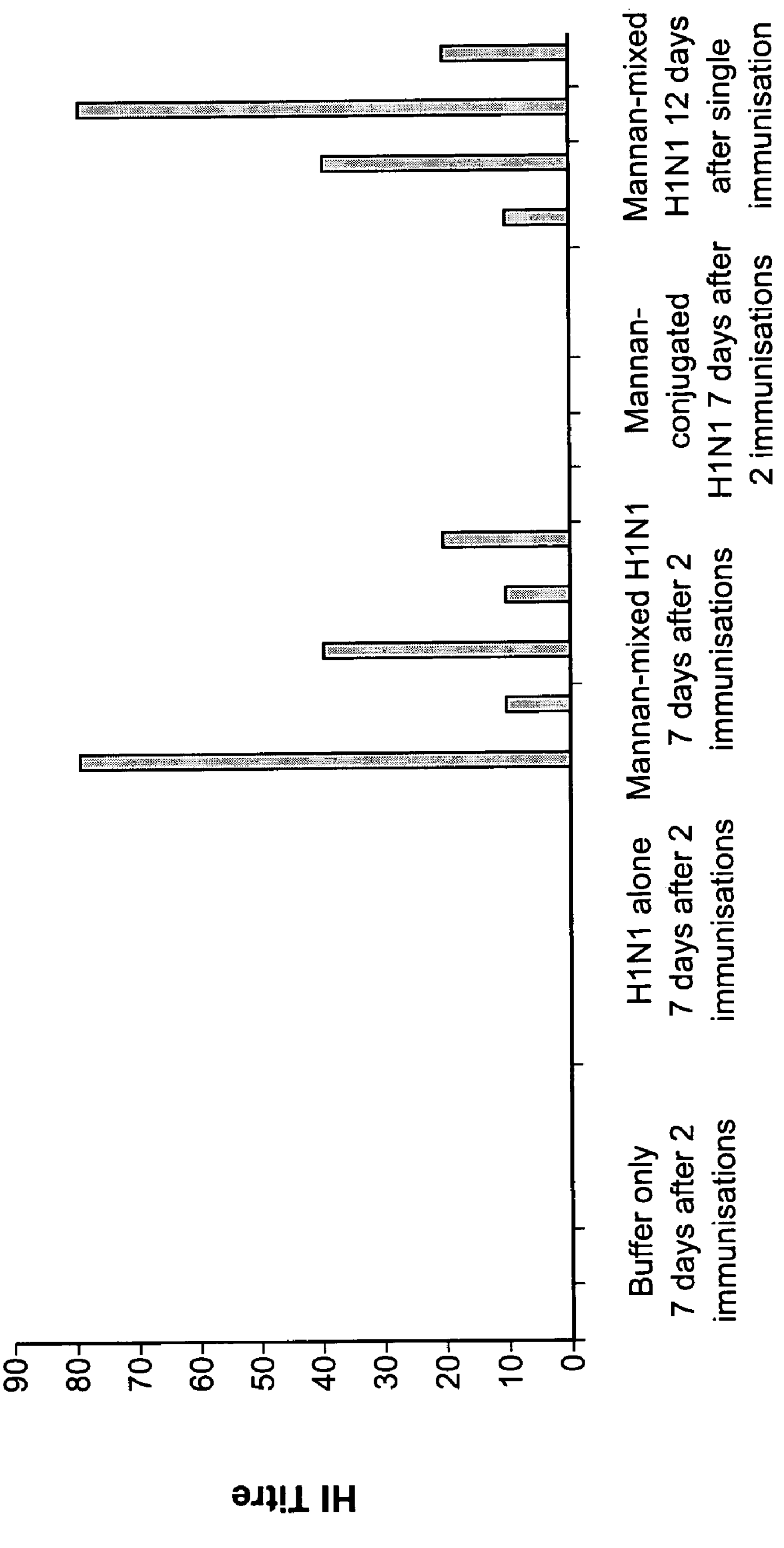
Figure 13:
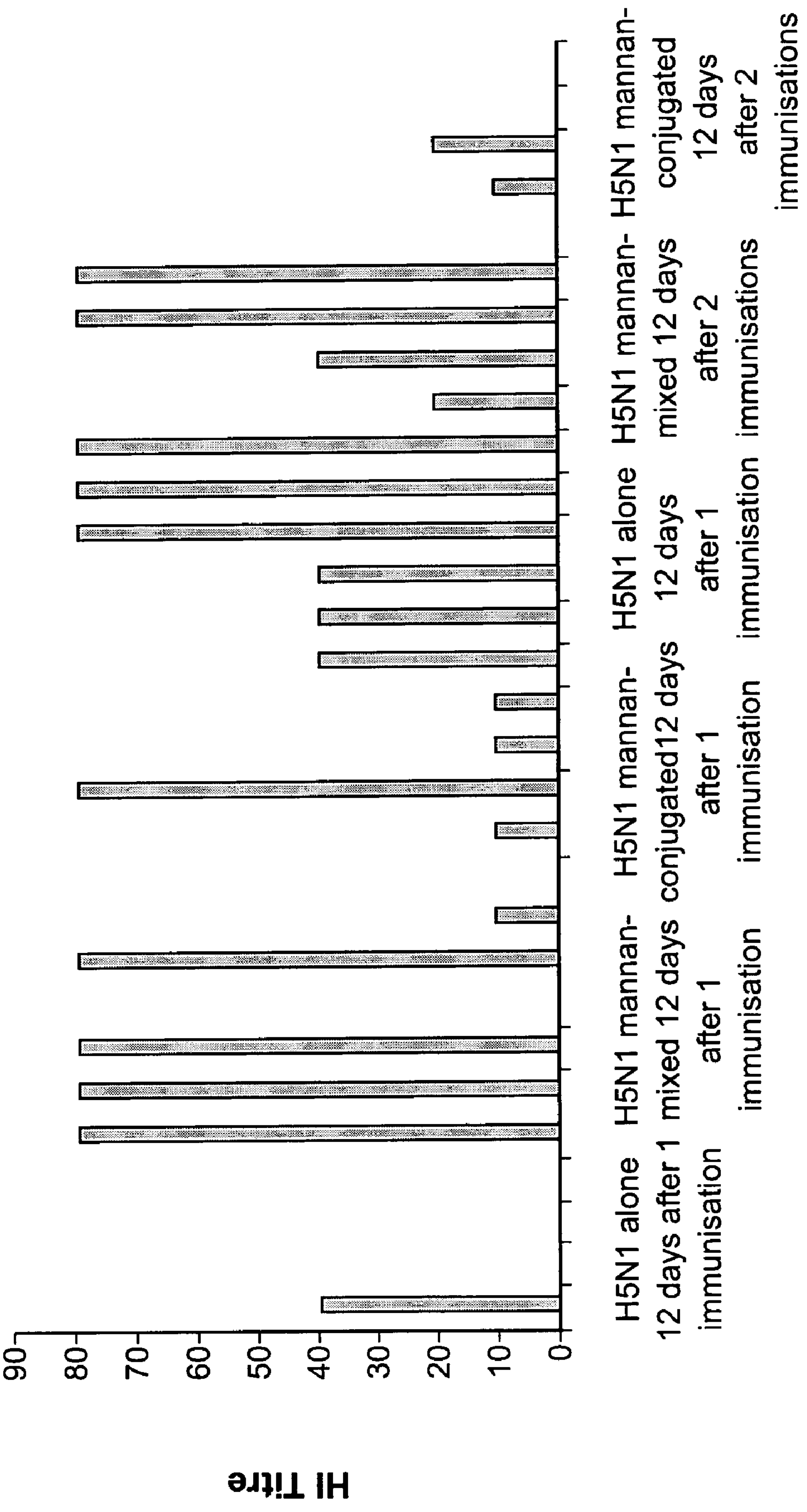

Referring to FIG. 13, it can be seen that the admixture of H5N1 and mannan administered in a dose of 10 μg intranasally produced quite high HI titres.

Example 9

Dosage Sparing Amounts of H1N1 and H5N1

Experiments were conducted to determine whether increasing the amount of mannan in admixed flu virus mannan compositions could reduce the dosage amount of the flu virus.

Figure 14:
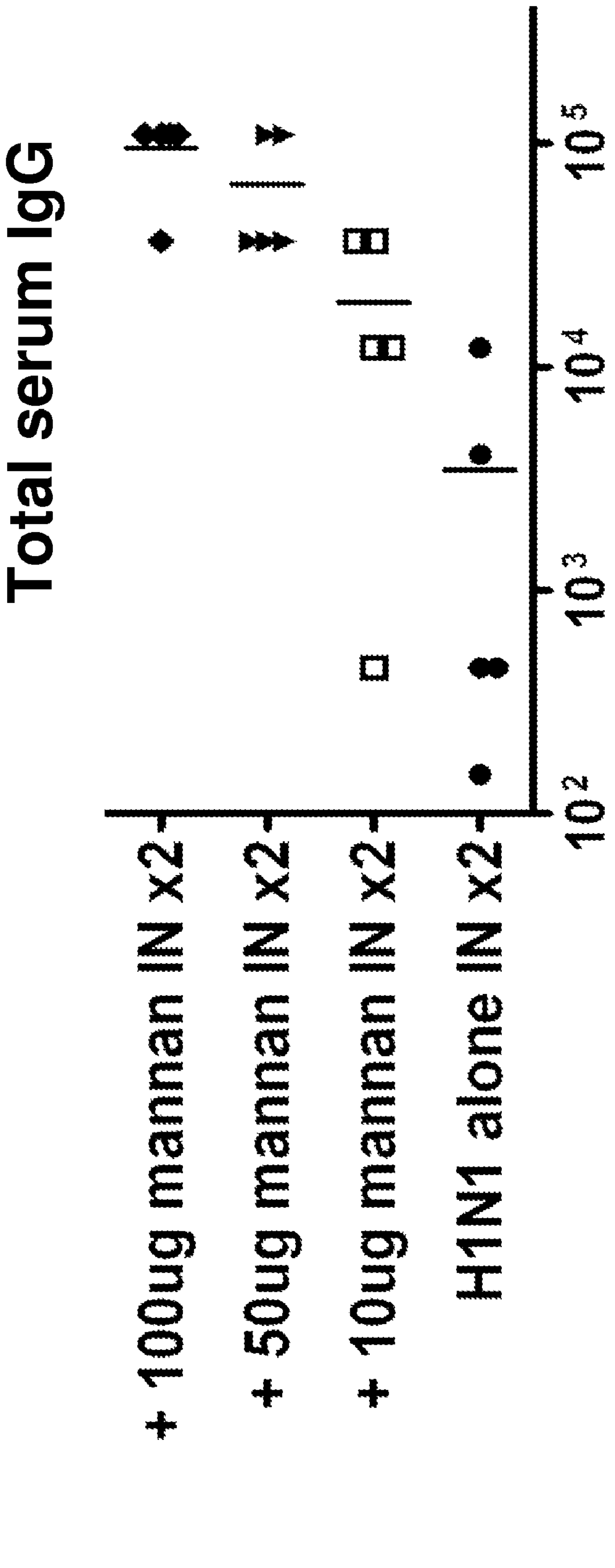
FIG. 14 shows the results of serum IgG from mice intranasally administered with flu virus mannan admixtures with various amounts of mannan and a low (i.e. 1 μg) amount of strain H1N1 influenza (flu) virus.

The results shown in FIG. 14 showed that admixtures comprising 1 μg of H1N1 and various amounts of mannan (i.e. 10 μg, 50 μg and 100 μg) administered intranasally, produced strong IgG immune responses (particularly at 50 μg and 100 μg amounts of mannan).

Figure 15:
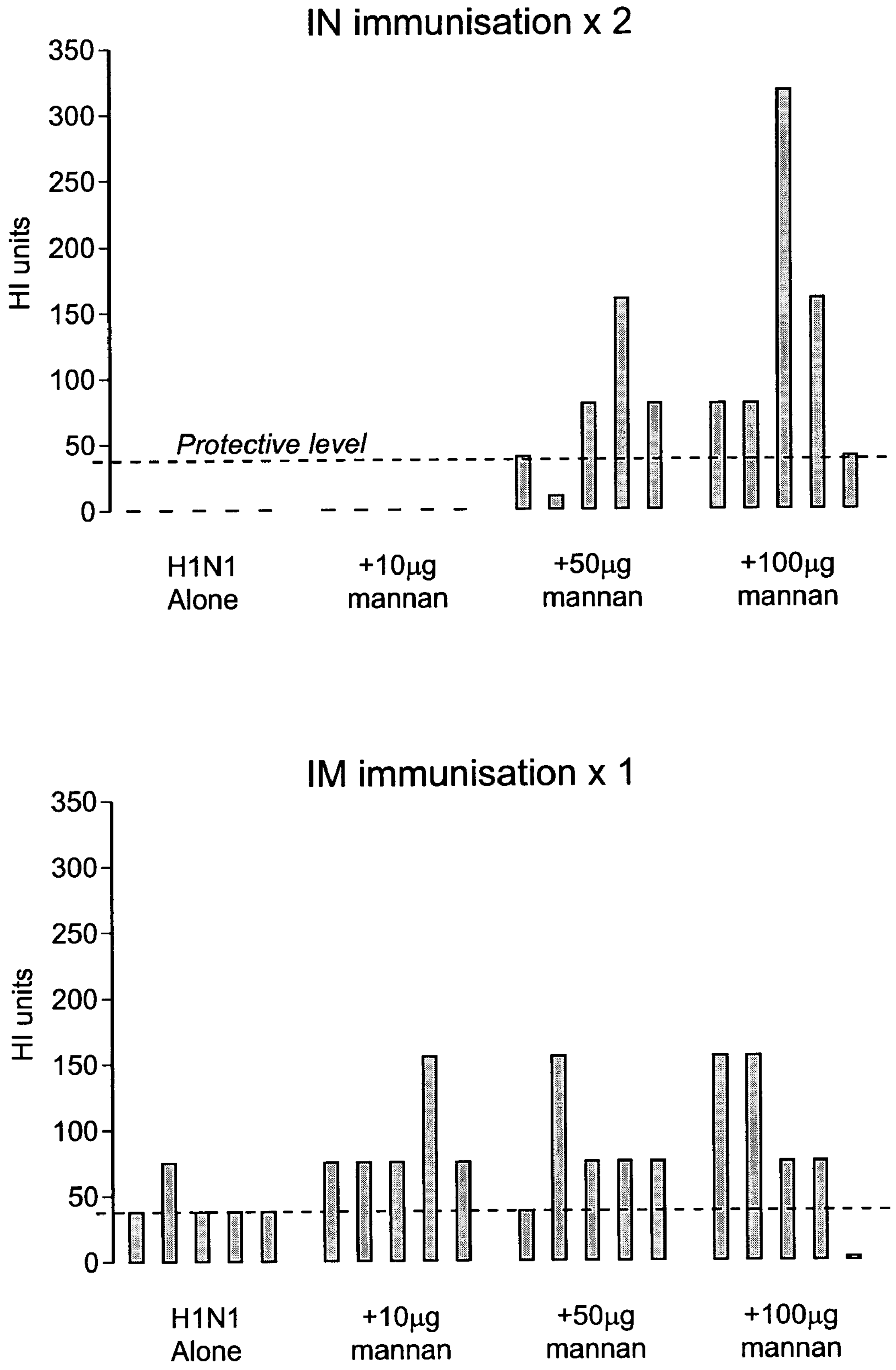
FIG. 15 shows serum HI after intranasal administration with flu virus mannan admixtures with various amounts of mannan and a low amount of strain H1N1 influenza (flu) virus.

Using HI assays as described above, it was also found that the use of low amount of flu virus nevertheless indicated that a protective immune response was produced (FIG. 15).

Figure 16:
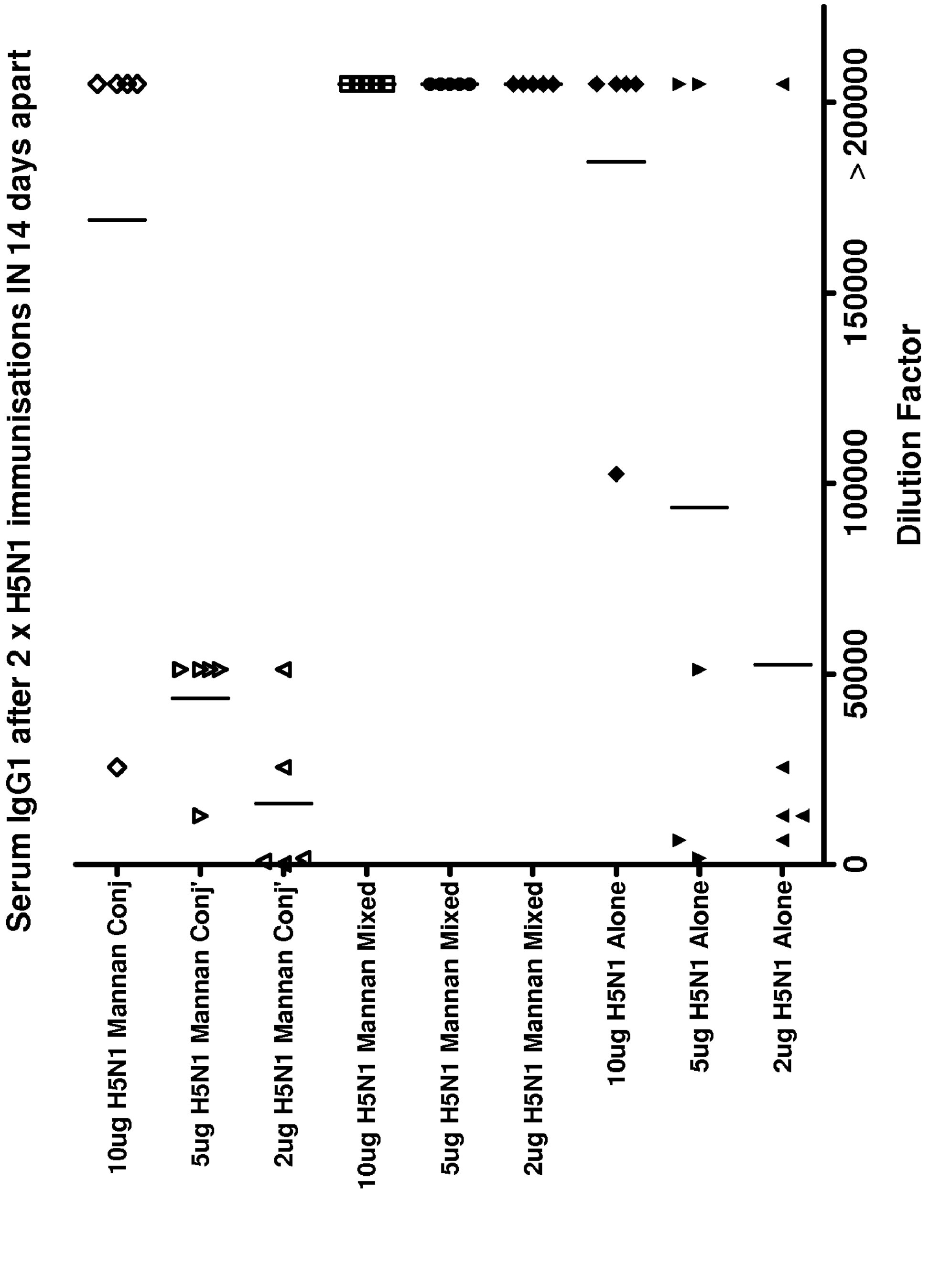
FIG. 16 shows serum IgG1 levels in mice following intranasal administration of various amounts of strain H5N1 influenza (flu) virus in admixture with mannan (amount of mannan to flu virus ratio was 1:10)
Figure 17:
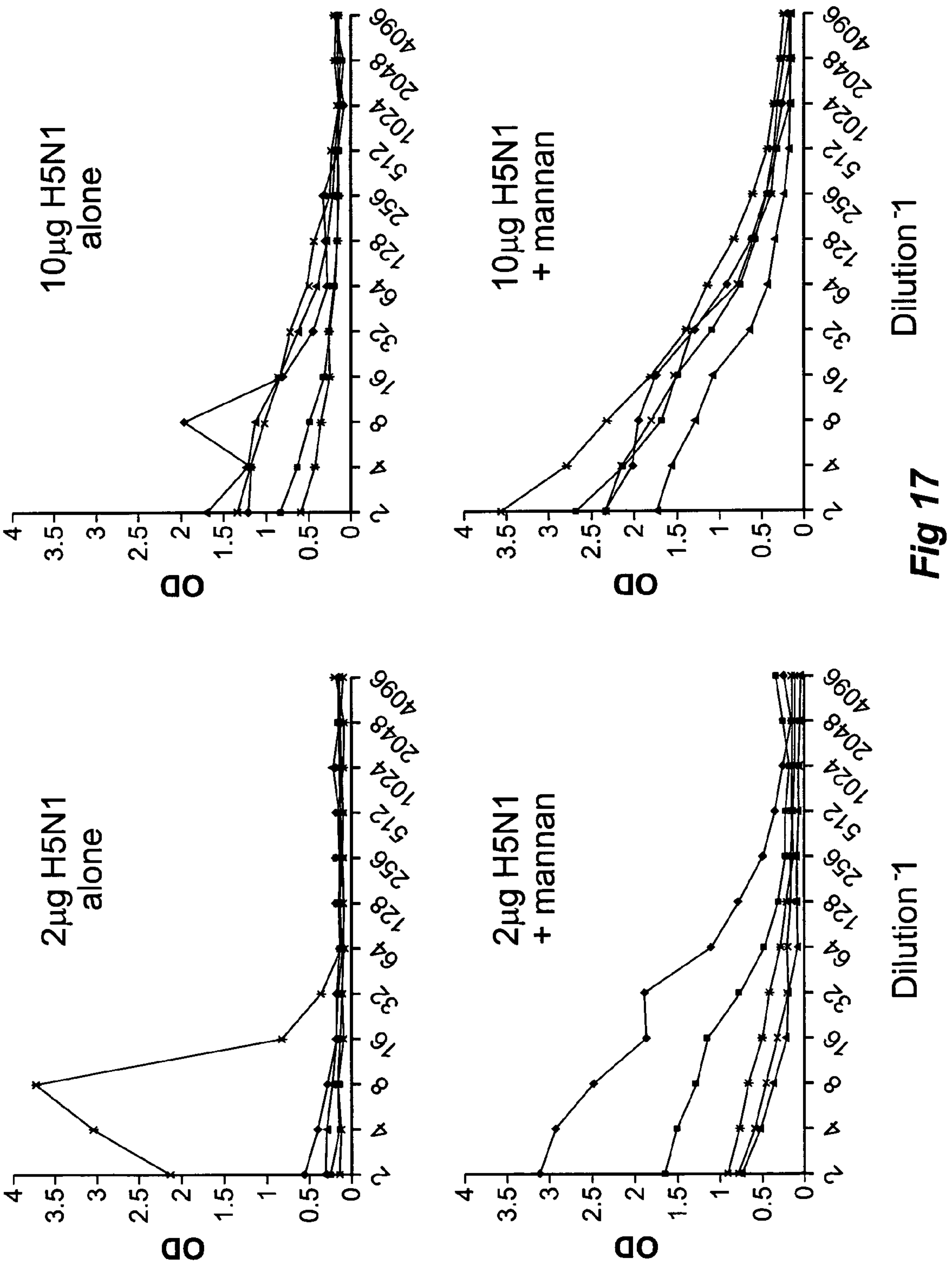
FIG. 17 shows lung IgA levels in mice following intranasal administration of various amounts of strain H5N1 influenza (flu) virus in admixture with mannan (amount of mannan to flu virus ratio was 1:10).

Similar experiments were conducted with strain H5N1 influenza virus; the outcome of which was the finding that similarly low levels of the flu virus (≦2 μg) could be used (FIGS. 16 and 17).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

[1] Williams R. C., and R. J. Gibbons. 1972. Inhibition of bacterial adherence by secretory immunoglobulin A: a mechanism of antigen disposal. Science 177: 697-699.

[2] Hajishengallis G., E. Nikolova, and M. W. Russell. 1992. Inhibition of Streptococcus mutans adherence to saliva-coated hydroxyapatite by human secretory immunoglobulin A (S-IgA) antibodies to cell surface protein antigen I/II: reversal by IgA1 protease cleavage. Infect Immun 60: 5057-5064.

[3] Gilbert J. V., A. G. Plaut, B. Longmaid, and M. E. Lamm. 1983. Inhibition of microbial IgA proteases by human secretory IgA and serum. Mol Immunol 20: 1039-1049.

[4] Outlaw M. C., and N. J. Dimmock. 1990. Mechanisms of neutralization of influenza virus on mouse tracheal epithelial cells by mouse monoclonal polymeric IgA and polyclonal IgM directed against the viral haemagglutinin. J Gen Virol 71: 69-76.

[5] Elson C. O., and Ealding W. 1984. Generalized systemic and mucosal immunity in mice after mucosal stimulation with cholera toxin. J. Immunol 132: 2736-2741.

[6] de Hann L., Verweij W., Agsteribbe E., and Wilschut J. 1998. The role of ADP-ribosylation and G(M)1-binding activity in the mucosal immunogenicity and adjuvanticity of Escherichia coli heat-labile enterotoxin and Vibrio cholerae cholera toxin. Immunol Cell Biol 76: 270-279.

[7] Hamajima K, Sasaki S, Fukushima J, et al 1998, Clin Immunol Immunopathol 88 (2): 205-210.

[8] Sasaki S, Hamajima K, Fukushima J, et al 1998, Infect Immunol 66 (2): 823-826.

[9] Robert-Guroff M, 1990, Int Rev Immunol 7: 15-30.

[10] Apostolopoulos V., B. E. Loveland, G. A. Pietersz, and I. F. McKenzie. 1995. CTL in mice immunized with human mucin 1 are MHC-restricted. J Immunol 155: 5089-5094.

[11] Apostolopoulos V., G. A. Pietersz, B. E. Loveland, M. S. Sandrin, and I. F. McKenzie. 1995. Oxidative/reductive conjugation of mannan to antigen selects for T1 or T2 immune responses. Proc Natl Acad Sci USA 92: 10128-10132.

[12] Karanikas V., L. A. Hwang, J. Pearson, C. S. Ong, V. Apostolopoulos, H. Vaughan, P. X. Xing, G. Jamieson, G. Pietersz, B. Tait, R. Broadbent, G. Thynne, and I. F. McKenzie. 1997. Antibody and T cell responses of patients with adenocarcinoma immunized with mannan-MUC1 fusion protein. J Clin Invest 100: 2783-2792.

[13] Apostolopoulos V P. G. A., Siamon G, Martinez-Pomares L, McKenzie IFC. 2000. Alhehyde-mannan antigen complexes target the MHC Class I antigen presentation pathways. Eur J Immunol 30, 1714-1723.

[14] Davenport F. M., Hennessy A. V., Brandon F. M., Webster R. G., Barrett C. D. (Jr), and Lease G. O. "Comparison of serologic and febrile responses in human vaccination with influenza A viruses or their haemagglutinins" J. Lab. Clin. Med. 1964, 63, 5-13.

The invention claimed is:

1. A vaccine composition comprising a carbohydrate polymer comprising mannose and influenza virus (flu) antigen(s) in admixture.

2. The composition of claim 1, wherein the flu antigen(s) are derived from human, avian or equine influenza virus.

3. The composition of claim 1, wherein the flu antigen (s) is a whole inactivated influenza virus.

4. The composition of claim 3, wherein the virus is H1N1 or H5N1.

5. The composition of claim 4, wherein the amount of the virus is ≦2 μg per dosage unit.

6. The composition of claim 4, wherein the amount of the virus is ≦0.5 μg per dosage unit.

7. The composition of claim 1, wherein the carbohydrate polymer comprising mannose is mannan.

8. The composition of claim 7, wherein the mannan is oxidised.

9. The composition of claim 1, wherein the composition is adapted to be administered at a mucosal site.

10. The composition of claim 9, wherein the composition is formulated for intranasal administration.

11. The composition of claim 1, wherein the composition is formulated for intramuscular administration.

12. A method of immunising a subject, comprising the step of administering a composition according to claim 1.

13. The method of claim 12, wherein the subject is a human.

14. The composition of claim 2, wherein the carbohydrate polymer comprising mannose is mannan.

15. The composition of claim 3, wherein the carbohydrate polymer comprising mannose is mannan.

16. The method of claim 12, wherein the composition is administered intranasally.

17. The method of claim 12, wherein the composition is administered intramuscularly.

18. The method of claim 12, wherein the carbohydrate polymer comprising mannose is mannan.

19. The method of claim 18, wherein the mannan is oxidised.

20. The method of claim 12, wherein the step of administering the composition is conducted by priming intramuscular administration, and boosting by intranasal administration.

* * * * *